United States Patent
Gumbrecht et al.

(10) Patent No.: US 8,062,502 B2
(45) Date of Patent: Nov. 22, 2011

(54) ARRANGEMENT AND METHOD FOR DETECTING SMALL SUBSTANCE CONCENTRATIONS

(75) Inventors: Walter Gumbrecht, Herzogenaurach (DE); Peter Paulicka, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 362 days.

(21) Appl. No.: 11/905,252

(22) Filed: Sep. 28, 2007

(65) Prior Publication Data

US 2008/0087555 A1    Apr. 17, 2008

(30) Foreign Application Priority Data

Sep. 29, 2006  (DE) .................. 10 2006 046 776

(51) Int. Cl.
- *G01N 27/26* (2006.01)
- *C12Q 1/68* (2006.01)
- *C07H 21/02* (2006.01)
- *C07H 21/04* (2006.01)

(52) U.S. Cl. .............. 205/793.5; 204/400; 422/68.1; 435/6; 435/7.1; 435/287.2; 536/23.1; 536/24.3

(58) Field of Classification Search .......... 435/6, 7.92, 435/7.1, 287.2; 205/775, 793.5, 779; 204/400, 204/403.01–403.15; 422/68.1; 536/23.1, 536/24.3

See application file for complete search history.

(56) References Cited

U.S. PATENT DOCUMENTS

| | | | |
|---|---|---|---|
| 7,488,578 B2 * | 2/2009 | Gumbrecht et al. ............. 435/6 |
| 2001/0003426 A1 * | 6/2001 | Matter et al. ................. 324/698 |
| 2002/0132351 A1 * | 9/2002 | Szecsody ....................... 436/25 |
| 2004/0029203 A1 * | 2/2004 | Gumbrecht et al. .......... 435/7.92 |
| 2004/0115663 A1 | 6/2004 | Berlin et al. |
| 2005/0003554 A1 * | 1/2005 | Brasseur ....................... 436/172 |
| 2008/0099347 A1 * | 5/2008 | Barlag et al. ................ 205/793.5 |

FOREIGN PATENT DOCUMENTS

| | | |
|---|---|---|
| DE | 100 58 397 | 6/2002 |
| DE | 100 58 394 C1 | 7/2002 |
| DE | 101 26 341 A1 | 12/2002 |
| DE | 10 2005 003 911 A1 | 8/2005 |
| JP | 4250812 A | 9/1992 |
| WO | WO2004/106546 | * 12/2004 |
| WO | WO/2005/073708 | * 11/2005 |

OTHER PUBLICATIONS

Paeschke et al., A stacked multichannel amperometric detection system, Micro Total Analysis Systems, pp. 249-254, 1995.*
United Kingdom Office Action.

* cited by examiner

*Primary Examiner* — Jeffrey T Barton
*Assistant Examiner* — Jennifer Dieterle
(74) *Attorney, Agent, or Firm* — Harness, Dickey & Pierce, P.L.C.

(57) ABSTRACT

In order to avoid problems caused by baseline drift, it is expedient in a method of an embodiment of the present application not to measure a signal rise in a detection space, but to allow a certain time period to elapse in order to enrich a detectable product (enrichment phase), then to measure a first detection signal, and to measure the baseline signal as second detection signal only after rinsing out the detection space and removing the enriched product. In at least one embodiment, the enriched product is not detected from a signal rise with reference to a baseline, but from a signal difference of first and second detection signals.

20 Claims, 4 Drawing Sheets

FIG 2
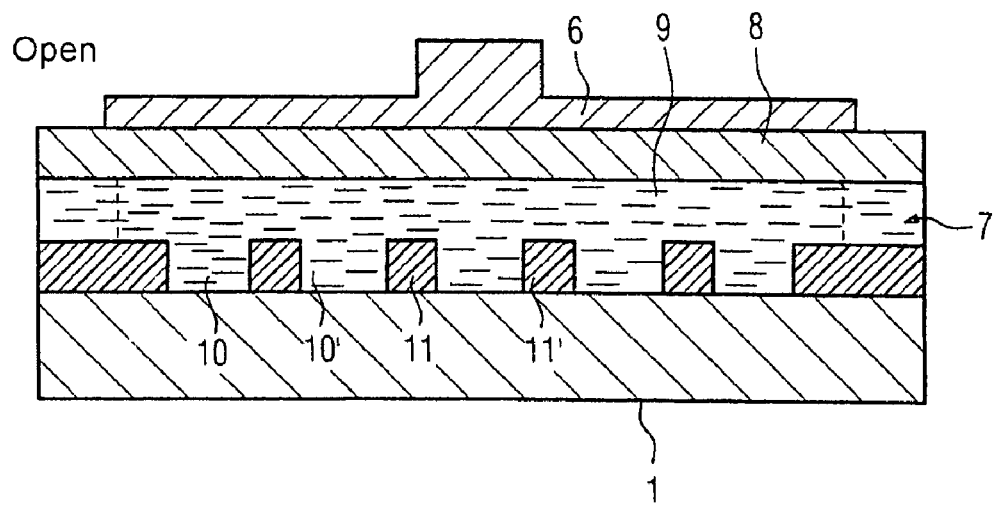
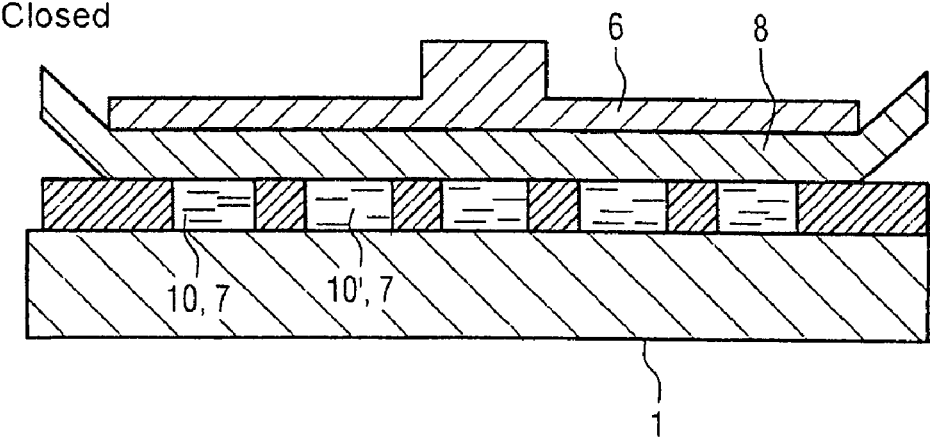

ARRANGEMENT AND METHOD FOR DETECTING SMALL SUBSTANCE CONCENTRATIONS

PRIORITY STATEMENT

The present application hereby claims priority under 35 U.S.C. §119 on German patent application number DE 10 2006 046 776.0 filed Sep. 29, 2006, the entire contents of which is hereby incorporated herein by reference.

FIELD

Embodiments of the invention generally relate to a method for detecting a detectable product that is enriched before measurement to increase the sensitivity of the method. Embodiments of the invention further generally relate to an arrangement for carrying out this method.

BACKGROUND

It is an aim of chemical and biochemical analytics to develop detection methods with an increased sensitivity. Sensitive and highly specific analytical methods based on molecular interactions, for example of nucleic acids or proteins, have been developed in biochemical analytics, in particular. Such methods are used, for example, in process analytics, in molecular diagnostics, in molecular biological research, in clinical diagnostics, in food analysis and in environmental analytics.

Patent DE 100 583 94 C1 describes an electrochemical sensor that can be used for nucleic acid analytics. This sensor has electrodes to which there is applied a microarray arrangement of catcher oligonucleotides that can specifically bind nucleic acids to be detected. These nucleic acids to be detected can be marked or labeled with an enzyme that converts a substrate to an electrochemically detectable product. The current rise can be measured at the electrodes upon the emergence of the product. To raise the sensitivity of this measurement method, DE 100 583 94 C1 teaches the use of small volume detection spaces in order to amplify the local increase in concentration of the electrochemically detectable product, and thus to raise the sensitivity.

The sensitivity of such measurement methods is limited, on the one hand, by signal noise and, on the other hand, by the so called baseline drift that leads to a shift in the baseline in the course of time such that in the event of very small analyte concentrations it is not possible to make any reliable statement relating to a signal rise with reference to the baseline. This problem of baseline drift occurs not only in electrochemical measurement methods, but also with other detection methods, for example optical, magnetic and other methods. Baseline drift is conditioned by a multiplicity of causes, for example by temperature fluctuations, by interface effects at the interface from sensor to sample volume, in particular when use is made of measuring electrodes on the basis of polarization effects on measuring electrodes and sample solution, and by other effects.

SUMMARY

In at least one embodiment, the present invention provides a detection method that enables measurement independently of baseline drift and/or provides a detection method that has a raised sensitivity with reference to known methods.

At least one embodiment of the invention is based on the idea that in order to avoid problems caused by baseline drift it is expedient not to measure a signal rise in a detection space, but to allow a certain time period to elapse in order to enrich a detectable product (enrichment phase), then to measure a first detection signal, and to measure the baseline signal as second detection signal only after rinsing out the detection space and removing the enriched product. It follows that the enriched product is not detected from a signal rise with reference to a baseline, but from a signal difference of first and second detection signals.

An inventive method for detecting a detectable product, of at least one embodiment, includes:
a) enriching the detectable product by an enrichment reaction in a detection space during a first time period;
b) acquiring a first detection signal of the detectable product during the first time period;
c) terminating the enrichment by rinsing the detectable product out from the detection space; and
d) acquiring a second detection signal after the rinsing out.

In accordance with at least one embodiment of the invention, the second detection signal is acquired subsequent to expiry of a second time period that begins with the rinsing out of the detection space, the first time period being longer than the second time period.

The enrichment reaction is a chemical reaction in which a substrate or educt is converted into a detectable product, the detectable product being enriched by the enrichment reaction in the course of time.

The first detection signal is preferably acquired at the end of the first time period.

The first time period is preferably at least three times as long as the second time period, with greater preference at least 10 times as long and, with even greater preference at least 20 times as long. The longer the first time period, the longer can the product be enriched, and the more sensitive is the measurement. It is also conceivable when detecting extremely low concentrations for the first time period to be 100 times and more longer than the second time period.

The product formed can be rinsed out from the detection space with a washing solution, but expediently with the same substrate solution that is introduced into the detection chamber before the enrichment time period begins. A baseline shift which is as small as possible is thereby ensured during measurement of the first and the second detection signals since, except for the product formed, the same solution is present in a detection space, and therefore the same chemical conditions are present at the sensor during the rinsing out. When the first time period (enrichment phase) before the acquisition of the first detection signal is sufficiently long, it is of no importance that in some circumstances new detectable product is already formed again in the detection space during the second time period (after the rinsing out and before acquisition of the second detection signal), since the second time period is comparatively short, and thus scarcely any new detectable product is formed. The second time period is preferably not longer than 5 s, with greater preference not longer than 3 s, and with even greater preference not longer than 1 s. Consequently, the first time period can be, for example, 10 s to 100 s or 1000 s and more. The length of the first time period is limited chiefly by the requirement to keep the total measuring time short.

In accordance with at least one embodiment of the present invention, detection signals are measured continuously during a measurement phase, the measurement phase including the transition from the first time period to the second, that is to say signals are measured continuously before, during and after the rinsing out operation. The first and second detection signals can then be selected from these continuously measured detection signals, the first and second detection signals preferably being selected such that a maximum difference is obtained between first and second detection signals.

In accordance with at least one embodiment of the present invention, the enrichment reaction is an enzymatically catalyzed reaction. Enzyme coupled detection methods are frequently used in biochemical analytics. The detectable product is preferably enriched by an enzyme that is coupled to an analyte to be detected.

The analyte to be detected is preferably a biological material, for example a cell, a cell constituent, a virus, a bacterium, a protein, a peptide or a nucleic acid. The product to be detected is preferably enriched by an enzyme that is coupled to an analyte to be detected or is coupled to the analyte by a detection reaction, for example by a covalent bond, by a complex bond, by a nucleic acid-nucleic acid interaction, a protein-protein interaction or a protein-nucleic acid interaction. It is also conceivable, alternatively, for an educt of the detectable product to be coupled to the analyte and to supply the detectable product by the enrichment reaction. It is preferred for the analyte to be detected to be bound to a solid phase in the detection space. The analyte to be detected is preferably bound to the solid phase in the detection space by a catcher molecule that specifically binds the analyte. This can be achieved, for example, by providing for the purpose of detecting analytes in the detection space a microarray of catcher molecules that can specifically bind analytes to be detected. This can, for example, be a microarray of oligonucleotides for detecting nucleic acid analytes, or an array of antibodies for detecting protein analytes.

In accordance with a further aspect of at least one embodiment of the present invention, the product is preferably detected electrochemically. However, it is likewise conceivable for the product to be detected by another detection principle, for example optically.

The detection space is preferably sealed during the first time period (enrichment phase) such that no exchange of fluid to the outside can take place. The detection space can be of trough-type design, for example, with the purpose of sealing being served by sealingly fitting, for example pressing on, a sealing layer over the trough rim. The detectable product formed is preferably rinsed out by connecting the detection space to a fluid reservoir and/or actuating a pump, the pump being able to pump a fluid for rinsing out into the detection space.

It has emerged that measuring at an electrochemical sensor is influenced by whether the detection space is in an open state or a closed one. Consequently, in accordance with a preferred aspect of the present invention the detection space is closed during an enrichment phase (first time period) such that the detectable product can be enriched in the detection space. To rinse out the detectable product, the detection space is opened or a fluid connection is produced to a fluid reservoir such that the detection space can be rinsed out, the detection space subsequently being resealed, and the second detection signal being measured or acquired, in turn, with the detection space closed at the end of the second time period.

In accordance with at least one embodiment of the present invention, it is possible to form from the first and second detection signals a difference or a quotient that can be used to quantify the product. Furthermore, the quantification can be performed by means of known methods, for example drawing a calibration curve with the aid of a standard of known concentration.

In accordance with a further aspect of at least one embodiment of the inventive method, during the first time period (enrichment phase) a number of first detection signals are acquired and a signal strength of the first detection signal is extrapolated up to the instant of the acquisition of the second signal. The sensitivity of the method can be further increased by keeping the volume of the detection space small, and/or by keeping the ratio of volume of the detection space to an active surface on which the product enrichment reaction takes place small. It is therefore preferred for the total volume of the detection space, particularly during the enrichment phase, to be 1 µl or less, preferably 10 nl or less, most preferably 1 nl or less. Furthermore, it is preferred for the quotient of volume of the detection space to the active surface on which the enrichment reaction takes place to be 1 mm or less, preferably 0.1 mm or less, more preferably 0.01 mm or less. The inventive method is thus provided for use with small detection spaces, in particular. At least one embodiment of the method is preferably carried out in microfluidic devices, for example in microfluidic cartridges, such as are described in DE 10111457A1, for example, the entire contents of which is incorporated herein by reference.

At least one embodiment of the invention further relates to an arrangement for carrying out the above described inventive method, the arrangement including:
a) a detection space with means for detecting a detectable product;
b) means for rinsing out the detection space with a fluid; and
c) a controller that is designed to acquire a first signal, to actuate the means for rinsing out the detection space, and to acquire a second detection signal after rinsing out of the detection space.

The detection space preferably has a microarray arrangement of catcher molecules that can bind a biological material. It is preferably possible to seal the detection space selectively, for example by pressing a sealing layer onto an opening in the detection space. The detection space can preferably be selectively connected to a fluid reservoir.

The detection means preferably comprise an electrochemical sensor. This can be designed in the form of an electrode arrangement such as described, for example, in documents DE 100 583 97 A1, DE 101 263 41 A1 or DE 100 583 94 C1.

The controller can comprise a microprocessor controller and can, for example, be computer aided. The controller can be used to fix the length of the first time period and of the second time period, and to fix the instants for the measurement of all the detection signals.

At least one embodiment of the inventive arrangement can have a plurality of detection spaces. These detection spaces can be separable from one another. The detection spaces can be applied as planar arrangement to a silicon substrate, the reaction spaces preferably being separated from one another by a polymer layer applied to silicon.

BRIEF DESCRIPTION OF THE DRAWINGS

Further advantages, features and properties of the present invention are explained with the aid of example embodiments and the appended drawings, in which.

FIG. 2 shows a schematic illustration of an arrangement of detection spaces that can be used in an embodiment of the inventive method;

DETAILED DESCRIPTION OF THE EXAMPLE EMBODIMENTS

Figure 1:
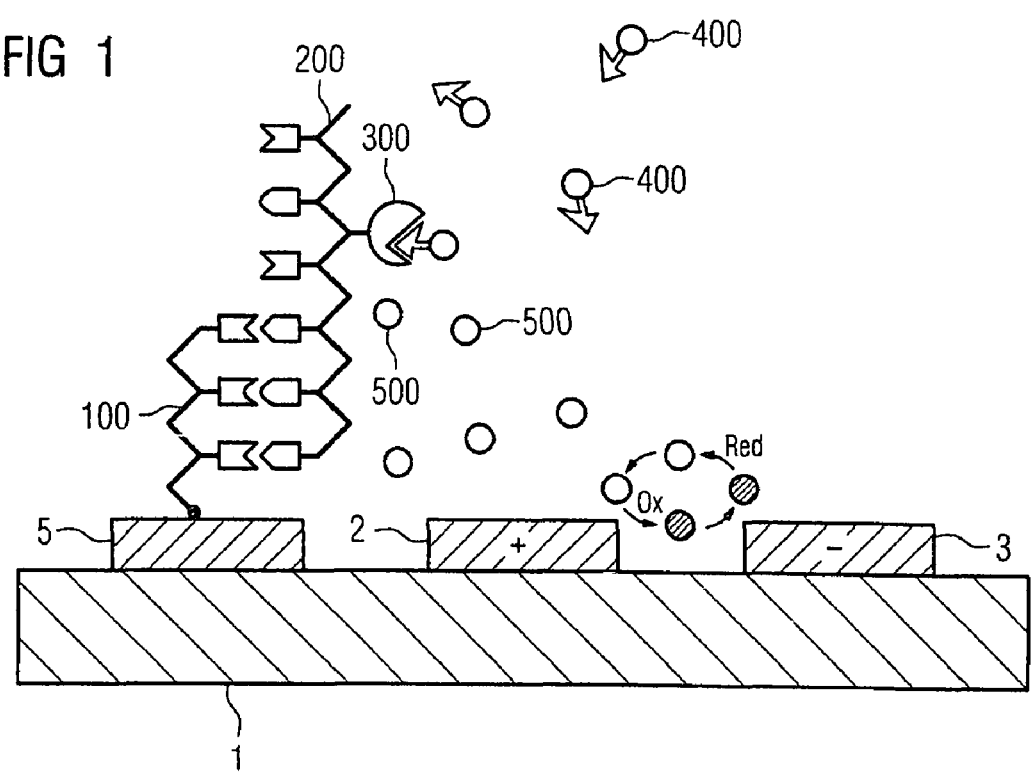
FIG. 1 shows a schematic illustration of an enrichment reaction of a detectable product that can be used in an embodiment of the inventive method.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

Shown schematically in FIG. 1 is an enrichment and detection reaction that can be used in the inventive method. The detection electrodes 2, 3 are applied to a substrate 1 that can be a silicon chip, for example, as is a carrier layer 5 on which DNA oligonucleotides 100 are immobilized. It is also conceivable for the oligonucleotides to be immobilized directly on the electrodes. The oligonucleotides 100 serve as catcher molecules for an analyte 200 that is to be detected and is a nucleic acid molecule which can be specifically bound by the catcher molecule 100. The nucleic acid molecule 200 is labeled with an enzyme 300. The enzyme 300 converts a substrate 400 into a detectable product 500. Use may be made as enzyme 300 of an alkaline phosphatase that as substrate 400 can hydrolyze the substance p-aminophenyl phosphate to the detectable product 400, p-aminophenol. p-aminophenol is oxidized in a known way on the electrode 2 to form quinoneimine, and the quinoneimine formed is reduced back to form p-aminophenol on the counter electrode 3. Upon application of a voltage, this process, known as redox cycling, leads to a measurable current rise at the electrodes 2, 3.

At the start of the measurement operation, the detection chamber is flooded with a substrate solution and subsequently sealed. During a first time period, that is to say the enrichment phase, the enzyme continuously converts the substrate such that the detectable product is enriched. The detection space is sealed during this enrichment phase. A first detection signal is then measured. Subsequently, the detection space is opened and flooded with fresh substrate solution. As a result, detectable product that emerges is rinsed away, and a drop in the current flow comes about at the electrodes 2, 3. Measurement is now performed a second time. A second detection signal is obtained as a result, the first detection signal now being compared not against the original baseline, but against the second detection signal.

FIG. 2 shows an arrangement of detection spaces 10, 10, that are formed on a silicon chip 1 and are separated by walls 11, 11'. The detection spaces 10, 10, can be produced by applying a polymer layer and incorporating depressions, the walls 11, 11' consisting of the polymer material not removed.

The detection spaces 10, 10' can, in FIG. 2, be terminated by a housing upper part 8 by means of a mechanical die 6. The housing upper part can be formed as sealing layer from an elastic material, for example a silicone material, or preferably from a rigid material for example polycarbonate that is elastically mounted (suspended). In the case of this embodiment, the detection spaces 10, 10' are firstly filled with substrate solution 7 by continuous flow with an open housing upper part 8, the space 9 above the detection spaces 10, 10' constituting a reservoir for the substrate solution. After filling of the detection spaces 10, 10' with substrate solution 7, the die 6 is used to place the housing upper part 8, which can consist of a silicone diaphragm, or preferably of a rigid material, for example polycarbonate, that is elastically mounted (suspended), onto the walls 11, 11' which are composed of polyamide, for example, and the reaction chambers 10, 10' are thereby terminated. It is now possible for the enrichment phase, in which detectable product is formed in the detection spaces 10, 10' and is enriched, to take place during a first time period. The first detection signal is acquired toward the end of the enrichment phase. Subsequently, the detection spaces 10, 10' are opened by withdrawing the die 6, fresh substrate solution 7 flowing back and the detectable product formed being rinsed out of the detection spaces 10, 10' because of eddies. Rinsing out can likewise be backed up and/or implemented by actuating or switching on a pump that feeds fresh substrate solution. A second detection signal is now acquired. It is possible to infer the presence of formed detectable product from the difference between first detection signal and second detection signal.

The acquisition of the detection signals and the actuation of the die are implemented by a controller (not shown). This controller is a component of the inventive arrangement.

Figure 3:
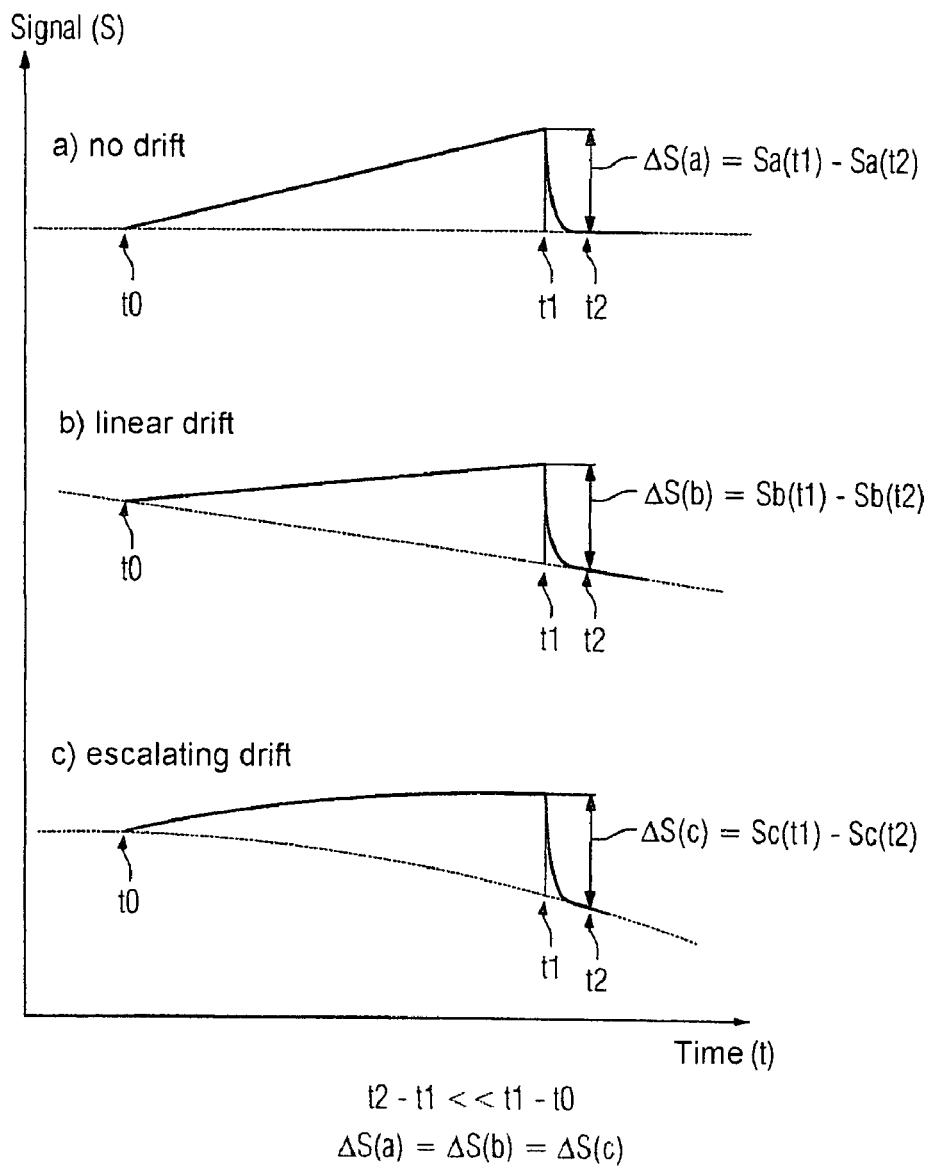
FIG. 3 shows a curve, plotted against time, of signal strength that illustrates the effect of an embodiment of the inventive method.

The mode of operation of an embodiment of the inventive method is illustrated in FIG. 3 against time with the aid of graphic illustrations of the signal strength. The method is carried out in an arrangement, illustrated as above, with an electrochemical sensor. Shown in curve 3a) is a measurement in the case of which no baseline drift has occurred. At the instant t0, the detection space is sealed and the enrichment phase begins. At the instant t1, a first detection signal is acquired, and the detection chamber is subsequently rinsed out. Since the detectable product is thereby rinsed away from the electrodes, the current strength drops, and a second detection signal is acquired at the instant t2. The signal strength difference $\Delta S$ is yielded from $\Delta S = S(t1) - S(t2)$.

A situation with linear baseline drift is shown in curve 3b), that is to say the baseline drops continuously during measurement. At the instant t0, the detection space is sealed and the enrichment phase begins. Because of the baseline drift, in case 3b) the rise in the signal, (that is to say the gradient of the curve) is less than in the case of 3a). Measurement and rinsing are now performed again in the way described above, and then measurement is carried out at t2. Although the signal rise is weaker overall during the measurement, the signal strength difference $\Delta S$ (b) is just as high as the signal strength difference $\Delta S$ (a).

A situation with escalating baseline drift is illustrated in curve 3c), that is to say the baseline firstly drops slowly, and then ever more steeply over the course of time. Here, as well, the gradient of the signal strength is less than in the case of curve 3a), while the signal strength difference $\Delta S$ (c) is nevertheless just as large as the signal strength difference $\Delta S$ (a).

It is to be seen straightaway that errors caused by baseline drift are compensated by using an embodiment of this method. Furthermore, a much stronger signal is provided by the enrichment of the detectable product, and so the inventive method is very sensitive.

In the case of the electrochemical sensor described in the above example embodiment, a background noise of the order of magnitude of 1 pA is customary, that is to say the signal can vary in this order of magnitude. Current rises of a few nA/s can be measured in the event of detection of a relatively large analyte concentration. At the same time, the baseline drift moves in the order of a few 10 pA/s. This baseline drift is therefore not problematic given a signal of a number of nA/s. However, in the event of detection of very small analyte quantities it can be that the signal rise is of the order of magnitude of only a few 10 to a few 100 pA/s, and thus that the signal rise is of a similar order of magnitude to the fluctuation in the baseline because of the baseline drift. This leads to intolerable measuring errors. However, errors owing to baseline drift are compensated upon use of the inventive method. Furthermore, an embodiment of the inventive method enables an increase in sensitivity by a number of orders of magnitude with reference to methods in which the rise of the signal is measured.

Figure 4:
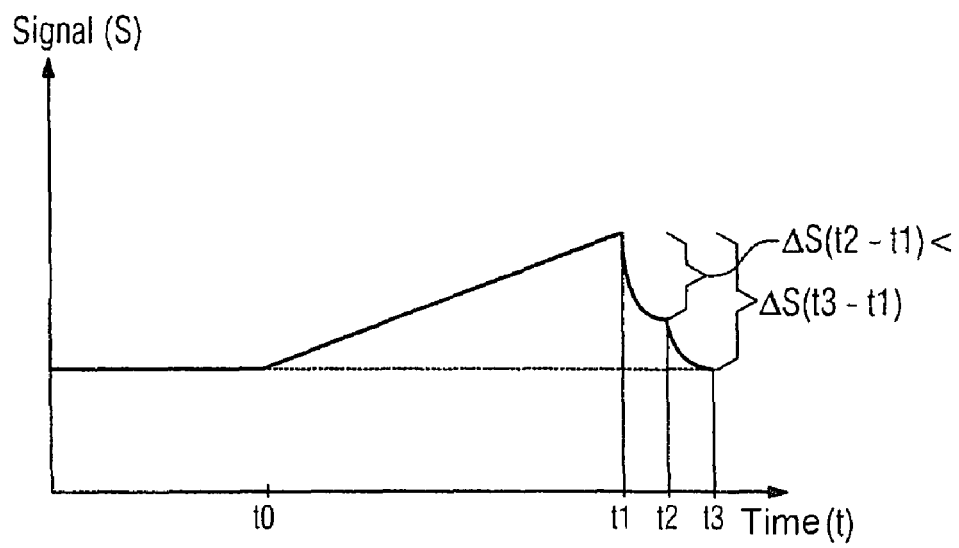
FIG. 4 shows a curve, plotted against time, of signal strength that illustrates a further embodiment of an embodiment of the inventive method.

Illustrated schematically in FIG. 4 is the action of a further embodiment of the inventive method that leads to a further raised sensitivity. During the measurement, there is present at the electrodes 2, 3 (see FIG. 1) a voltage that builds up an electric field. The detection space is sealed during the measurement of the first detection signal that is to say, the die 6 illustrated in FIG. 2 is lowered such that the silicone diaphragm 5 closes the reaction spaces 10, 10'. The lowering of the die influences the electric field formed between the electrodes, and leads to a slight lowering of the signal strength. A raised signal strength is measured with an open detection space, irrespective of the concentration of detectable product, since now die and silicone diaphragm no longer interfere with the electric field formed between the electrodes 2, 3.

It is preferred in accordance with the development of an embodiment of the method of the invention firstly to open the detection space in order to enable the product formed to be rinsed out, then to lower the die 6 again and thus to reclose the detection space, and only then to acquire the second detection signal. This is illustrated schematically in the curve of FIG. 4: at the instant t1 the first detection signal is acquired, and subsequently the detection space is opened such that detectable product is rinsed out from the detection space. At the instant t2, the detection space is resealed, and the second detection signal is not acquired until the instant t3. The signal strength difference $\Delta S$ (t2–t1) is smaller than the signal strength distance $\Delta S$ (t3–t1). A further increase in sensitivity is thereby possible.

Figure 5:
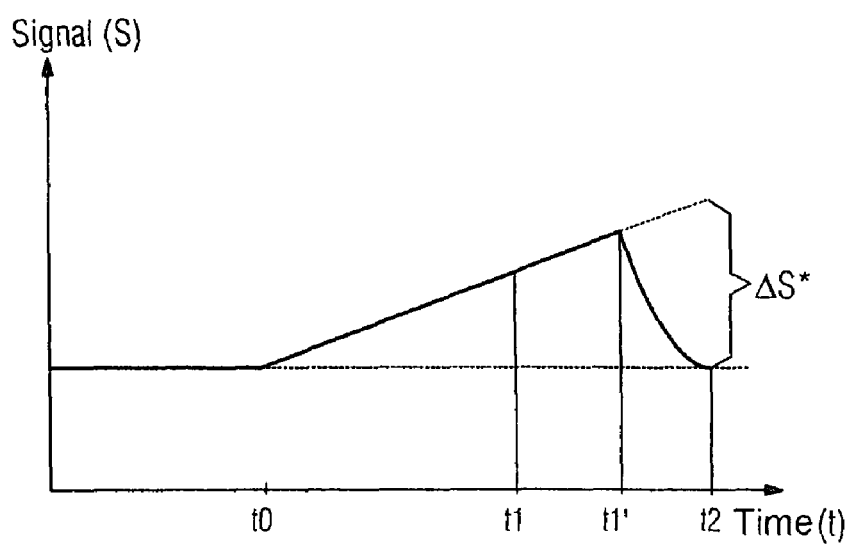
FIG. 5 shows a curve, plotted against time, of signal strength that illustrates yet a further embodiment of the inventive method.

The action of a further embodiment of the inventive method is illustrated schematically in FIG. 5. During the enrichment phase between the instants t0 and t1', a number of first detection signals t1 and t1' are acquired. Extrapolated starting therefrom is a signal strength that would be present if the enrichment phase up to the instant t2 at which the second detector signal is acquired were detectable if the rinsing out had not taken place. The difference between the extrapolated signal strength and the signal strength actually measured at t2 after rinsing out of the detection chamber is used as signal strength difference $\Delta S$. It is thereby possible to achieve a further increase in sensitivity.

It is emphasized that the example embodiments illustrated are only exemplary and explanatory. The invention is not to be limited to the electrochemical detection described, but can be used for any method in which a detectable product can be enriched during an enrichment phase irrespective of the detection principle. Further changes and modifications of the inventive method and the inventive arrangement are conceivable and possible to the extent they are covered by the patent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for detecting a detectable product, comprising:
    filling a detection space with a substrate solution;
    enriching a detectable product by an enrichment reaction in the detection space during a first time period corresponding to an enrichment period;
    acquiring a first detection signal of the detectable product following the enriching that occurs during the first time period via a controller;
    terminating the enriching during the first time period by rinsing the detectable product out from the detection space with the substrate solution;
    acquiring a baseline signal as a second detection signal via the controller after the rinsing out, the second detection signal being acquired from the substrate solution in the detection space, wherein the first detection signal is acquired at the end of the first time period and the second detection signal is acquired subsequent to expiration of a second time period that begins with the rinsing out of the detection space, the first time period being relatively longer than the second time period; and
    determining an amount of detectable product from a signal difference between the first and the second detection signals.

2. The method as claimed in claim 1, wherein the first time period is at least ten times as long as the second time period.

3. The method according to claim 1, wherein the product is detected electrochemically.

4. The method as claimed in claim 1, wherein the rinsing out is performed by connecting the detection space to a fluid reservoir.

5. The method as claimed in claim 1, further including quantifying the product by comparing at least one of a difference and a quotient from first and second signals.

6. The method as claimed in claim 1, wherein, during the first time period, a number of first detection signals are acquired and a signal strength is extrapolated up to the instant of the acquisition of the second signal.

7. The method as claimed in claim 1, wherein the detection is performed in a detection space that has an active surface on which the product enrichment reaction takes place and the quotient of volume to active surface is 0.1 mm or less.

8. The method as claimed in claim 1, further including comparing the first detection signal against the second detection signal.

9. The method as claimed in claim 1, further including measuring the first detection signal and the second detection signal, the second detection signal serving as the baseline signal.

10. The method as claimed in claim 1, wherein detection signals are measured continuously during a measurement phase including the transition from the first time period to the second one, the first and second detection signals being selected from the detection signals acquired during the measurement phase.

11. The method as claimed in claim 10, wherein the first and second detection signals are selected such that a maximum signal strength difference results from first and second detection signals.

12. The method as claimed in claim 1, wherein the enriching is performed by sealing the detection space.

13. The method as claimed in claim 12, wherein the rinsing out is performed by at least one of opening the detection space and actuating a pump.

14. The method as claimed in claim 13, wherein the second detection signal is acquired after resealing of the detection space.

15. The method as claimed in claim 1, wherein the enrichment reaction is an enzymatically catalyzed reaction.

16. The method as claimed in claim 15, wherein the enriching is performed by an enzyme that is coupled to an analyte to be detected.

17. The method as claimed in claim 16, wherein the analyte to be detected is a biological material.

18. The method as claimed in claim 16, wherein the analyte to be detected is bound to a solid phase in the detection space.

19. The method as claimed in claim 18, wherein the analyte to be detected is bound to a solid phase in the detection space by a catcher molecule that specifically binds the analyte.

20. A method for detecting a detectable product, comprising: filling a detection space with a substrate solution;
    enriching a detectable product by an enrichment reaction in the detection space during a first time period;
    acquiring a first detection signal of the detectable product during the first time period via a controller;
    terminating the enriching during the first time period by rinsing the detectable product out from the detection space with the substrate solution;
    acquiring a baseline signal as a second detection signal via the controller after the rinsing out, wherein the first detection signal is acquired at the end of the first time period and the second detection signal is acquired subsequent to expiration of a second time period that begins with the rinsing out of the detection space, the first time period being relatively longer than the second time period, wherein
    detection signals are measured continuously during a measurement phase including the transition from the first time period to the second one, the first and second detection signals being selected from the detection signals acquired during the measurement phase, and
    wherein the first and second detection signals are selected such that a maximum signal strength difference results from first and second detection signals.

* * * * *